United States Patent [19]
Willis et al.

[11] 4,109,662
[45] Aug. 29, 1978

[54] FLAVORING COMPOSITIONS CONTAINING ALKYL-2,3-DIHYDRO-3(1'-HYDROXYALKYLIDENE)-2-OXO-5-ALKYL-FURAN-4-CARBOXYLATES

[75] Inventors: Brian J. Willis, Bergenfield, N.J.; Frank Fischetti, Jr., Flushing; Robert G. Eilerman, Hempstead, both of N.Y.

[73] Assignee: Fritzsche Dodge & Olcott Inc., New York, N.Y.

[21] Appl. No.: 698,742

[22] Filed: Jun. 22, 1976

Related U.S. Application Data

[63] Continuation-in-part of Ser. No. 601,482, Aug. 4, 1975, abandoned.

[51] Int. Cl.² .......................... A24B 3/12; A24D 1/18
[52] U.S. Cl. ..................................... 131/2; 131/17 R; 131/144; 426/536
[58] Field of Search ...................... 131/2, 144, 17, 15; 426/536

[56] References Cited

U.S. PATENT DOCUMENTS

| | | | |
|---|---|---|---|
| 3,381,690 | 5/1968 | Schumacher | 131/17 R |
| 3,931,824 | 1/1976 | Miano et al. | 131/2 |

OTHER PUBLICATIONS

Perfume and Flavor Chemicals, vol. I by Arctander, published by author in 1969, article 1412 & 1413 cited.

*Primary Examiner*—Robert W. Michell
*Assistant Examiner*—V. Millin
*Attorney, Agent, or Firm*—Frank M. Nolan

[57] ABSTRACT

The flavor compositions of this invention include alkyl-2,3-dihydro-3(1'-hydroxyalkylidene)-2-oxo-5-alkyl-furan-4-carboxylates which significantly enhance the flavor component or components of flavor compositions. For example, butterscotch flavors are materially improved in smoothness and certain fruit flavors are given greater richness and ripeness.

13 Claims, No Drawings

FLAVORING COMPOSITIONS CONTAINING ALKYL-2,3-DIHYDRO-3(1'-HYDROXYALK-YLIDENE)-2-OXO-5-ALKYL-FURAN-4-CARBOXYLATES

This application is a continuation-in-part of U.S. Pat. application Ser. No. 601,482 of Willis et al., filed Aug. 4, 1975, now abandoned.

This invention relates to flavor compositions and more particularly to flavor compositions containing an alkyl-2,3-dihydro-3(1'-hydroxyalkylidene)-2-oxo-5-alkyl-furan-4-carboxylate.

It is well known that synthetic flavor enhancers such as Maltol, Ethyl Maltol, and 4-hydroxy-2,5-dimethyl-3(2H)-furanone are useful as flavor enhancers. However, such flavor enhancers are very expensive and increase the cost of products in which they are used.

In accordance with one feature of this invention, an alkyl-2,3-dihydro-3(1'-hydroxyalkylidene)-2-oxo-5-alkyl-furan-4-carboxylate is added to flavor components to impart a significantly enhanced flavor to a wide variety of flavor components. For example, butterscotch flavors are materially improved in smoothness. Strawberry flavors are given a striking freshness. Banana flavors are rounded out to give the flavor of a ripe banana. When added to smoking tobacco or synthetic tobacco, the resulting product is increased in sweetness, the taste of the smoke is softened and the flow of saliva is increased, which lessens dryness of the mouth during smoking. When added to cough syrup containing theophylline, the flavor enhancer of this invention covers up the bitter taste. This flavor enhancer can also be used to replace part of the sugar content of a wide variety of sweetened beverages and foods, producing excellent flavor at lower cost.

Alkyl-2,3-dihydro-3(1'-hydroxyalkylidene)-2-oxo-5-alkyl-furan-4-carboxylates employed in the flavor compositions of this invention have the formula:

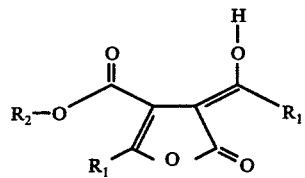

in which $R_1$ is a straight or branched chain alkyl having less than 6 carbon atoms, and $R_2$ is a straight or branched chain alkyl having less than 7 carbon atoms, cyclopentyl or cyclohexyl.

Examples of $R_1$ are methyl, ethyl, propyl, isopropyl, butyl, isobutyl, amyl and isoamyl.

Examples of $R_2$ are methyl, ethyl, propyl, isopropyl, butyl, isobutyl, amyl, isoamyl, hexyl or isohexyl.

$R_1$ and $R_2$ may be the same or different.

The alkyl-2,3-dihydro-3(1'-hydroxyalkylidene)-2-oxo-5-alkyl-furan-4-carboxylates may be prepared by the general methods of Knorr, Ber. 1889, 22, 158.

The flavor compositions of this invention comprise at least 0.0025% by weight of one or more alkyl-2,3-dihydro-3(1'-hydroxyalkylidene)-2-oxo-5-alkyl-furan-4-carboxylates. The amount of alkyl-2,3-dihydro-3(1'-hydroxyalkylidene)-2-oxo-5-alkyl-furan-4-carboxylate may vary within wide ranges such as 0.0001% to 30% by weight. More advantageously the range may be between 0.001% and 20% by weight of the flavor composition and preferably between 0.0025% and 5% by weight of the flavor composition.

Examples of flavor components of the flavor compositions of this invention are flavor mixtures per se such as pineapple, butterscotch, banana, and strawberry; foodstuffs such as meats, protein sources, fruits, cereals and other comestibles; beverages such as soft drinks, wines, alcoholic drinks, carbonated beverages; smoking tobacco; liquid medicaments such as cough syrups; and sugar substitutes in a wide range of edible or drinkable products.

In accordance with another feature of this invention, certain alkyl-2,3-dihydro-3(1'-hydroxyalkylidene)-2-oxo-5-alkyl-furan-4-carboxylates are new and novel. Such new and novel carboxylates significantly enhance the flavor components of the compositions of this invention. The new and novel carboxylates have the following formula:

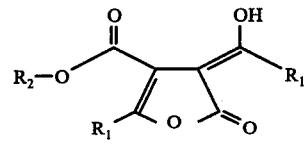

in which $R_1$ is a straight or branched chain alkyl having more than 1 and less than 6 carbon atoms, and $R_2$ is a straight or branched chain alkyl having more than 1 and less than 7 carbon atoms, cyclopentyl or cyclohexyl.

Examples of $R_1$ are ethyl, propyl, isopropyl, butyl, isobutyl, amyl and isoamyl.

Examples of $R_2$ are ethyl, propyl, isobutyl, amyl, hexyl and cyclopentyl.

$R_1$ and $R_2$ may be the same or different.

The new and novel carboxylates may be produced by the general method of Knorr, Ber. 1889, 22, 158.

A more comprehensive understanding of this invention is obtained from the following examples. Examples I and II show compositions produced with two levels of concentration of ethyl-2,3-dihydro-3(1'-hydroxyethylidene)-2-oxo-5-methyl-furan-4-carboxylate.

EXAMPLE I

| PINEAPPLE FLAVOR COMPOSITION | Parts by Weight | Parts by Weight |
|---|---|---|
| Allyl Cyclohexane Propionate | 1.4 | 1.4 |
| Geranyl Propionate | 0.5 | 0.5 |
| Allyl Caproate | 13.0 | 13.0 |
| Ethyl Iso Valerate | 1.0 | 1.0 |
| Ethyl Butyrate | 1.0 | 1.0 |
| Vanillin | 0.5 | 0.5 |
| Oil Orange | 1.0 | 1.0 |
| Maltol | 2.0 | 2.0 |
| Ethyl-2,3-Dihydro-3(1'-Hydroxyethylidene)-2-Oxo-5-Methyl-Furan-4-Carboxylate | 20.0 | 2.5 |
| Ethyl Alcohol 95% | 46.0 | 46.0 |
| Propylene Glycol | 13.6 | 31.1 |
| | 100.0 | 100.0 |

EXAMPLE II

| STRAWBERRY FLAVOR COMPOSITION | parts by Weight | Parts by Weight |
|---|---|---|
| Methoxy Phenyl Butanone | 1.0 | 1.0 |
| Ethyl Butyrate | 6.0 | 6.0 |
| Ethyl Iso Valerate | 2.0 | 2.0 |
| Benzyl Butyrate | 1.5 | 1.5 |

-continued
STRAWBERRY FLAVOR COMPOSITION

| | parts by Weight | Parts by Weight |
|---|---|---|
| Benzyl Iso Valerate | 0.5 | 0.5 |
| cis-3-Hexenol | 3.0 | 3.0 |
| Isobutyric Acid | 1.5 | 1.5 |
| Diacetyl | 0.2 | 0.2 |
| Butyl Phenylacetate | 0.4 | 0.4 |
| Acetaldehyde 50% in Ethanol | 0.2 | 0.2 |
| Benzyl Dipropyl Ketone | 0.2 | 0.2 |
| 2-Heptanone | 0.1 | 0.1 |
| Ethyl Methyl Phenyl Glycidate | 2.4 | 2.4 |
| Ethyl-2,3-Dihydro-3 (1'-Hydroxyethylidene)-2-Oxo-5-Methyl-Furan-4-Carboxylate | 30.0 | 5.0 |
| Propylene Glycol | 51.0 | 51.0 |
| Benzyl Alcohol | — | 25.0 |
| | 100.0 | 100.0 |

EXAMPLE III

BUTTERSCOTCH FLAVOR COMPOSITION

| | Parts by Weight |
|---|---|
| Ethyl-2,3-Dihydro-3 (1'-Hydroxyethylidene)-2-Oxo-5-Methyl-Furan-4-Carboxylate | 1.0 |
| Butyl Butyrolactate | 4.0 |
| Diacetyl | 0.2 |
| Ethyl Oleate | 2.0 |
| Ethyl Myristate | 0.5 |
| Vanillin | 1.5 |
| Acetoin | 0.3 |
| Phenylethanol | 0.2 |
| Butyric Acid | 0.1 |
| Ethyl Oxhydrate | 0.1 |
| Ethyl Maltol | 3.0 |
| Δ-Decalactone | 0.3 |
| γ-Nonalactone | 0.1 |
| Tincture Foenugreek | 0.4 |
| Methyl Cyclopentene-ol-one | 0.1 |
| Benzyl Alcohol | 26.0 |
| Propylene Glycol | 60.2 |
| | 100.0 |

EXAMPLE IV

BANANA FLAVOR COMPOSITION

| | Parts by Weight |
|---|---|
| Iso Amyl Acetate | 12.0 |
| Iso Amyl Butyrate | 10.0 |
| Benzyl Butyrate | 3.0 |
| Iso Amyl Iso Valerate | 2.0 |
| Ethyl Butyrate | 3.0 |
| Butyric Acid | 1.5 |
| Oil Lemon | 2.5 |
| Vanillin | 2.5 |
| Ethyl maltol | 0.5 |
| γ-Undecalactone | 0.4 |
| 4-(p-Hydroxyphenyl)-2-Butanone | 0.1 |
| Ethyl-2,3-Dihydro-3 (1'-Hydroxyethylidene)-2-Oxo-5-Methyl-Furan-4-Carboxylate | 10.0 |
| Propylene Glycol | 52.5 |
| | 100.0 |

EXAMPLE V

BUTTERSCOTCH FLAVOR

| | VA | VB |
|---|---|---|
| Butyl Butyrolactate | 4.0 | 4.0 |
| Diacetyl | 0.2 | 0.2 |
| Ethyl Oleate | 2.0 | 2.0 |
| Ethyl Myristate | 0.5 | 0.5 |
| Vanillin | 1.5 | 1.5 |
| Acetyl Methyl Carbinol | 0.3 | 0.3 |
| Phenykl Ethyl Alcohol | 0.2 | 0.2 |
| Butyric Acid | 0.1 | 0.1 |
| Ethyl Oxhydrate | 0.1 | 0.1 |
| Ethyl maltol | 3.0 | — |

-continued
BUTTERSCOTCH FLAVOR

| | VA | VB |
|---|---|---|
| Ethyl-2,3-Dihydro-3 (1'-Hydroxyethylidene)-2-Oxo-5-Methyl-Furan-4-Carboxylate | 1.0 | 5.0 |
| Δ-Decalactone | 0.3 | 0.3 |
| γ-Nonalactone | 0.1 | 0.1 |
| Tincture Foenugreek | 0.4 | 0.4 |
| Methyl Cyclopenten-ol-one | 0.1 | 0.1 |
| Benzyl Alcohol | 26.0 | 26.0 |
| Propylene Glycol | 60.2 | 59.2 |
| | 100.0 | 100.0 |

Formula VA contains Ethyl Maltol in addition to ethyl-2,3-dihydro-3(1'-hydroxyethylidene)-2-oxo-5-methyl-furan-4-carboxylate, while Formula VB contains only the carboxylate as a complete replacement for Ethyl Maltol. The butterscotch flavor achieved by Formula VB is richer and smoother.

The replacement proportion of Ethyl Maltol by ethyl-2,3-dihydro-3(1'-hydroxyethylidene)-2-oxo-5-methyl-furan-4-carboxylate is approximately one and one-half parts by weight of the carboxylate for one part by weight of Ethyl Maltol.

EXAMPLE VI

WINE FLAVOR COMPOSITION

The wine flavor composition is produced by initially adding 0.08 parts by weight of ethyl-2,3-dihydro-3(1'-hydroxyethylidene)-2-oxo-5-methyl-furan-4-carboxylate to 99.92 parts by weight of natural wine flavor. Four liquid ounces of the wine concentrate are added to one gallon of wine.

A wine flavor composition may also be produced by preparing a 1% by weight ethanol solution of ethyl-2,3-dihydro-3(1'-hydroxyethylidene)-2-oxo-5-methyl-furan-4-carboxylate and adding 0.32 fluid ounces of the solution to 1 gallon of wine. This is equivalent to 25 parts per million.

EXAMPLE VII

TOBACCO FLAVOR COMPOSITION

A 1% ethanol solution of ethyl-2,3-dihydro-3(1'-hydroxyethylidene)-2-oxo-5-methyl-furan-4-carboxylate is sprayed on smoking tobacco at the rate of 4 ounces of solution per 100 pounds of tobacco. After the alcohol is allowed to evaporate, a tobacco flavor composition results.

To produce a flavored tobacco which also contains synthetic tobacco, the procedure for the production of tobacco flavor composition heretofore described in this Example is repeated except that instead of employing smoking tobacco only, synthetic tobacco such as cellulose fibers, for example, the cellulose fibers sold by the Celanese Chemical Company under the trademark "CYTREL" or the cellulose fibers sold by Imperial Chemical Corporation under the trademark "POLYSTREP", is blended with the flavored tobacco in a ratio of approximately 1 to 1 by weight.

In a third procedure, a 1% ethanol solution of ethyl-2,3-dihydro-3(1'-hydroxyethylidene)-2-oxo-5-methyl-furan-4-carboxylate is sprayed on synthetic tobacco, such as cellulose fibers, at the rate of 4 ounces of solution to 100 pounds of synthetic tobacco. After the alcohol is allowed to evaporate, a tobacco flavor synthetic composition results.

Any one of the above tobacco flavor compositions may be used in cigarettes, producing a striking improvement in flavor.

Experiments were conducted with panatela cigars using ethyl-2,3-dihydro-3(1'-hydroxyisopentylidene)-2-oxo-5-isobutyl-furan-4-carboxylate as the flavor enhancer in 95% ethanol at the rate of 1.5 ounces of enhancer to 100 pounds of panatela cigars. The aroma and flavor of the smoke were significantly improved.

EXAMPLE VIII

CARBONATED SOFT DRINKS

A fruit flavor carbonated soft drink is produced by dissolving one ounce by weight of one of the flavor compositions such as described in Examples I or II in one gallon of sugar syrup. One ounce of the resulting mixture is added to about five ounces of carbonated water to produce six ounces of carbonated beverage.

The flavor composition containing 2.5% by weight of ethyl-2,3-dihydro-3(1'-hydroxyethylidene)-2-oxo-5-methyl-furan-4-carboxylate results in a level of 32 parts per million of ethyl-2,3-dihydro-3(1'-hydroxyethylidene)-2-oxo-5methyl-furan-4-carboxylate flavor enhancer in the total carbonated drink produced.

EXAMPLE IX

BUTTERSCOTCH FLAVOR COMPOSITION

A butterscotch composition containing a flavor enhancer in accordance with the teaching of the invention was prepared. For comparison, another composition containing the same ingredients but without the flavor enhancer was also prepared as a control. The formulas of the compositions are as follows:

|  | Parts by Weight (Control) | Parts by Weight |
|---|---|---|
| Butyl Butyrolactate | 4.0 | 4.0 |
| Diacetyl | 0.2 | 0.2 |
| Ethyl Oleate | 2.0 | 2.0 |
| Ethyl Myristate | 0.5 | 0.5 |
| Vanillin | 1.5 | 1.5 |
| Acetyl Methyl Carbinol | 0.3 | 0.3 |
| Phenyl Ethyl Alcohol | 0.2 | 0.2 |
| Butyric Acid | 0.1 | 0.1 |
| Ethyl Propionate | 0.1 | 0.1 |
| Ethyl Maltol | 3.0 | 3.0 |
| Δ-Decalactone | 0.3 | 0.3 |
| γ-Nonalactone | 0.1 | 0.1 |
| Methyl Para-Tertiary Butyl Phenylacetate in 1% alcohol) | 0.1 | 0.1 |
| Tincture Foenugreek | 0.4 | 0.4 |
| Cyclotene | 0.1 | 0.1 |
| Benzyl Alcohol | 27.1 | 27.1 |
| Propylene Glycol | 60.0 | 57.0 |
| Etnhyl-2,3-Dihydro-3 (1'-Hydroxypropylidene)-2-Oxo-5-Ethyl-Furan-4-Carboxylate | – | 3.0 |
|  | 100.0 | 100.0 |

The butterscotch composition containing the flavor enhancer had an immeasurably superior flavor over the control.

What is claimed is:

1. A smoking compositin comprising a smoking material and at least 0.0001% by weight of an alkyl-2,3-dihydro-3-(1'-hydroxyalkylidene)-2-oxo-5-alkyl-furan-4-carboxylate having the formula:

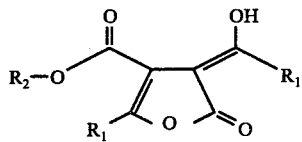

in which $R_1$ is a straight or branched chain alkyl having less than 6 carbon atoms and $R_2$ is a straight or branched chain alkyl having less than 7 carbon atoms, cyclopentyl or cyclohexyl.

2. A smoking composition of claim 1 in which the alkyl-2,3-dihydro-3(1'-hydroxyalkylidene)-2-oxo-5-alkyl-furan-4-carboxylate is ethyl-2,3-dihydro-3(1'-hydroxyethylidene)-2-oxo-5-methyl-furan-4-carboxylate.

3. A smoking composition of claim 1 in which the alkyl-2,3-dihydro-3(1'-hydroxyalkylidene)-2-oxo-5-alkyl-furan-4-carboxylate is ethyl-2,3-dihydro-3(1'-hydroxy-propylidene)-2-oxo-5-ethyl-furan-4-carboxylate.

4. A smoking composition of claim 1 in which the alkyl-2,3-dihydro-3(1'-hydroxyalkylidene)-2-oxo-5-alkyl-furan-4-carboxylate is ethyl-2,3dihydro-3(1'-hydroxyisopentylidene)-2-oxo-5-isobutyl-furan-4-carboxylate.

5. A smoking composition of claim 1 in which the alkyl-2,3-dihydro-3(1'-hydroxyalkylidene)-2-oxo-5-alkyl-furan-4-carboxylate present is 0.0001% to 30% by weight of the composition.

6. A smoking composition of claim 5 in which the alkyl-2,3-dihydro-3(1'-hydroxyalkylidene)-2-oxo-5-alkyl-furan-4-carboxylate is ethyl-2,3-dihydro-3(1'-hydroxyethylidene)-2-oxo-5-methyl-furan-4-carboxylate.

7. A smoking composition of claim 1 in which the alkyl-2,3-dihydro-3(1'-hydroxyalkylidene)-2-oxo-5-alkyl-furan-4-carboxylate present is 0.001% to 20% by weight of the composition.

8. A smoking composition of claim 7 in which the alkyl-2,3-dihydro-3(1'-hydroxyalkylidene)-2-oxo-5-alkyl-furan-4-carboxylate is ethyl-2,3-dihydro-3(1'-hydroxyethylidene)-2-oxo-5-methyl-furan-4-carboxylate.

9. A smoking composition of claim 1 in which the alkyl-2,3-dihydro-3(1'-hydroxyethylidene)-2-oxo-5-alkyl-furan-4-carboxylate present is 0.0025% to 5% by weight of the composition.

10. A smoking composition of claim 9 in which the alkyl-2,3-dihydro-3(1'-hydroxyalkylidene)-2-oxo-5-alkyl-furan-4-carboxylate is ethyl-2,3-dihydro-3(1'-hydroxyethylidene)-2-oxo-5-methyl-furan-4-carboxylate.

11. A smoking composition of claim 1 in which the smoking material is natural smoking tobacco.

12. A smoking composition of claim 1 in which the smoking material is synthetic smoking tobacco.

13. A smoking composition of claim 1 in which the smoking material is a mixture of natural smoking tobacco and synthetic smoking tobacco.

* * * * *